United States Patent
Teoh

(10) Patent No.: US 9,370,327 B2
(45) Date of Patent: Jun. 21, 2016

(54) MEDICAL DEVICES WITH RETRACTABLE NEEDLE AND RELATED METHODS

(71) Applicant: B. BRAUN MELSUNGEN AG, Melsungen (DE)

(72) Inventor: Teng Sun Teoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 14/605,711

(22) Filed: Jan. 26, 2015

(65) Prior Publication Data

US 2015/0208974 A1    Jul. 30, 2015

Related U.S. Application Data

(60) Provisional application No. 61/932,392, filed on Jan. 28, 2014.

(51) Int. Cl.
*A61B 5/15* (2006.01)
*A61B 5/154* (2006.01)
*A61M 5/178* (2006.01)

(52) U.S. Cl.
CPC .............. *A61B 5/154* (2013.01); *A61B 5/1438* (2013.01); *A61B 5/15003* (2013.01); *A61B 5/150389* (2013.01); *A61B 5/150488* (2013.01); *A61B 5/150572* (2013.01); *A61B 5/150633* (2013.01); *A61B 5/150732* (2013.01); *A61M 5/178* (2013.01); *Y10T 29/4984* (2015.01)

(58) Field of Classification Search
CPC ............. A61B 5/150656; A61B 5/154; A61B 5/150732; A61B 5/150282; A61B 5/1438; A61B 5/15003; A61B 5/150389; A61B 5/150572; A61B 5/150633; A61B 5/150488; A61M 5/178
USPC ................................... 600/576, 577; 604/110
See application file for complete search history.

(56) References Cited

U.S. PATENT DOCUMENTS

| | | | | |
|---|---|---|---|---|
| 5,997,507 A | * | 12/1999 | Dysarz | A61M 25/0631 604/110 |
| 6,156,013 A | | 12/2000 | Mahurkar | |
| 6,235,003 B1 | * | 5/2001 | Dysarz | A61M 5/3232 604/110 |
| 6,641,555 B1 | * | 11/2003 | Botich | A61B 5/1405 604/110 |
| 6,659,984 B2 | * | 12/2003 | Maclean Crawford | A61B 5/1405 604/110 |
| 6,669,671 B1 | | 12/2003 | Mohammad | |
| 7,481,797 B2 | | 1/2009 | Mahurkar | |
| 7,918,821 B2 | | 4/2011 | Mahurkar | |
| 8,147,455 B2 | | 4/2012 | Butts et al. | |
| 8,840,583 B2 | | 9/2014 | Jones | |
| 2007/0060840 A1 | * | 3/2007 | Conway | A61B 5/1405 600/576 |

FOREIGN PATENT DOCUMENTS

WO    WO 2007/022373 A2    2/2007

* cited by examiner

*Primary Examiner* — Theodore Stigell
(74) *Attorney, Agent, or Firm* — Klein, O'Neill & Singh, LLP

(57) ABSTRACT

Needle safety assemblies and related methods are disclosed. Exemplary needle safety assemblies include a needle with a sharpened tip attached directly or indirectly to an elongate tube having a proximal end that is constrained from proximal axial movement. An elongate shield with a distal end opening and a body extends over at least a portion of the elongate tube. A needle holder is coupled to the elongate shield and fixed axially. The needle holder has a proximal opening sized and shaped to receive a sampling device, such as a vacutainer. A tab having a pin extends radially outwardly from the elongate tube and through a slot formed with the elongate shield, which is movable to move the needle.

16 Claims, 3 Drawing Sheets

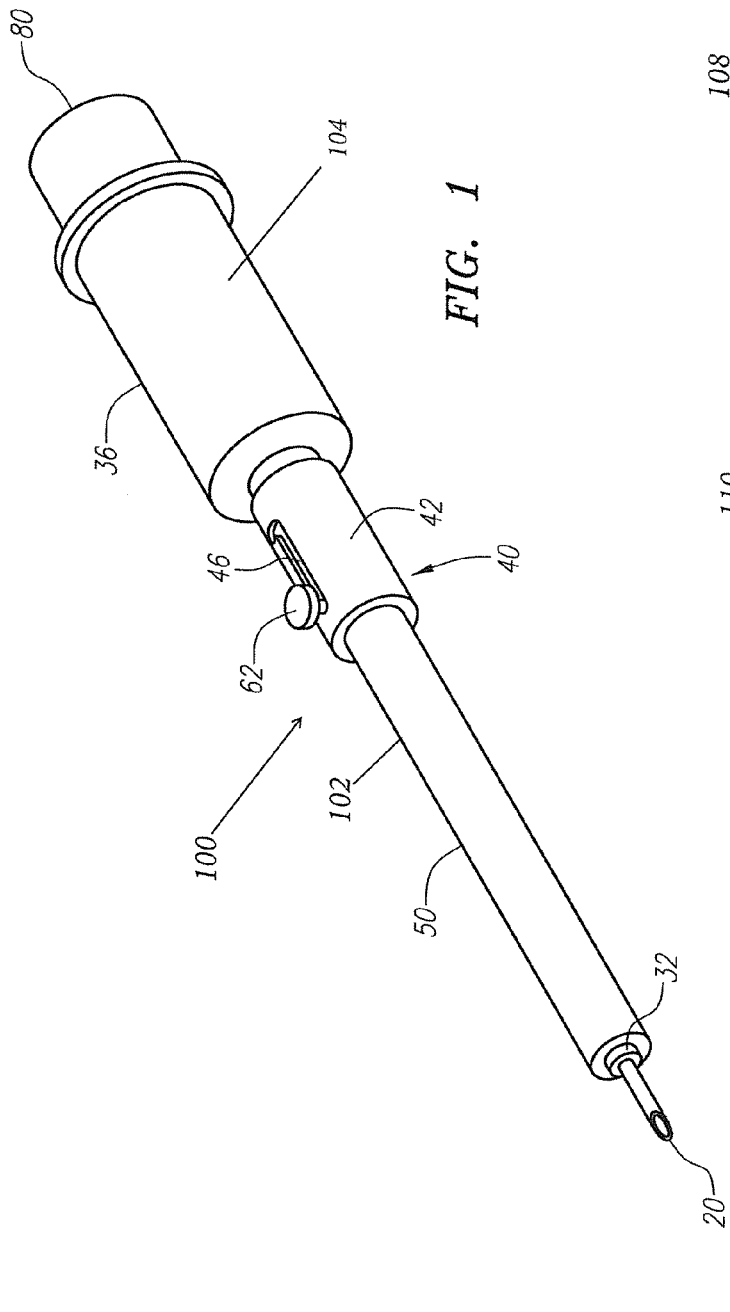
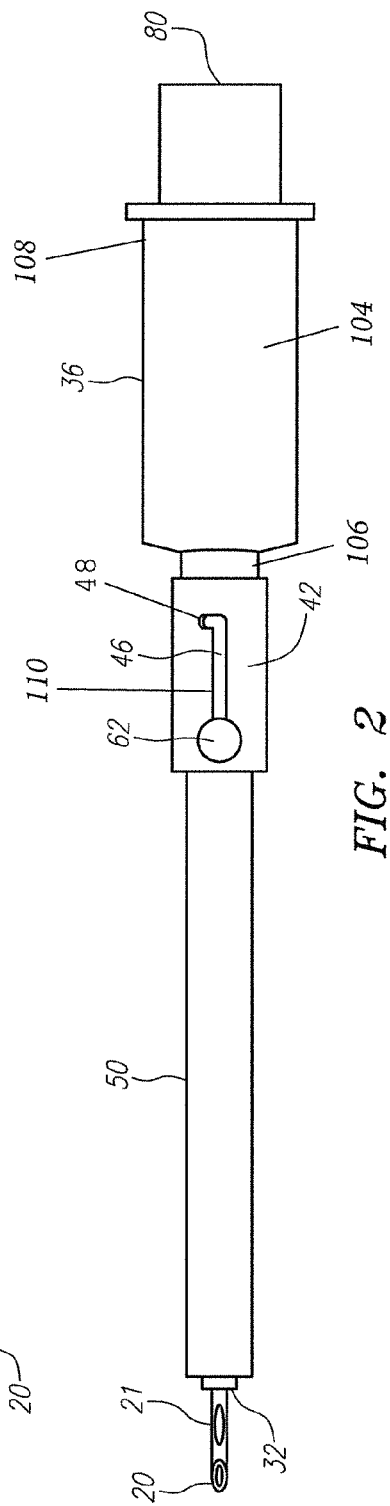

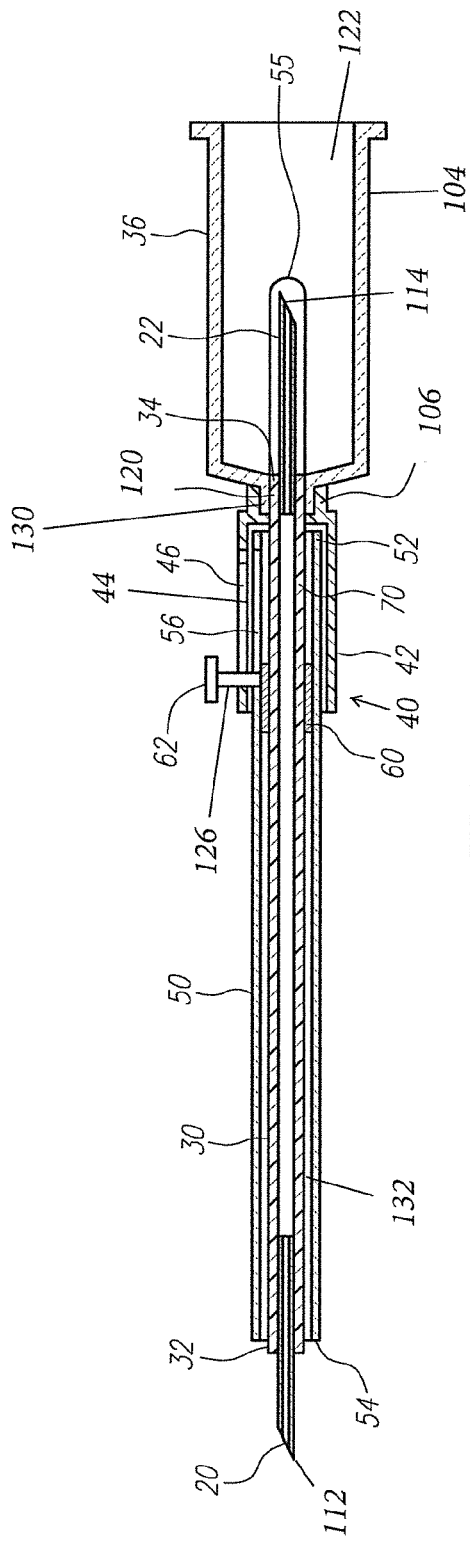
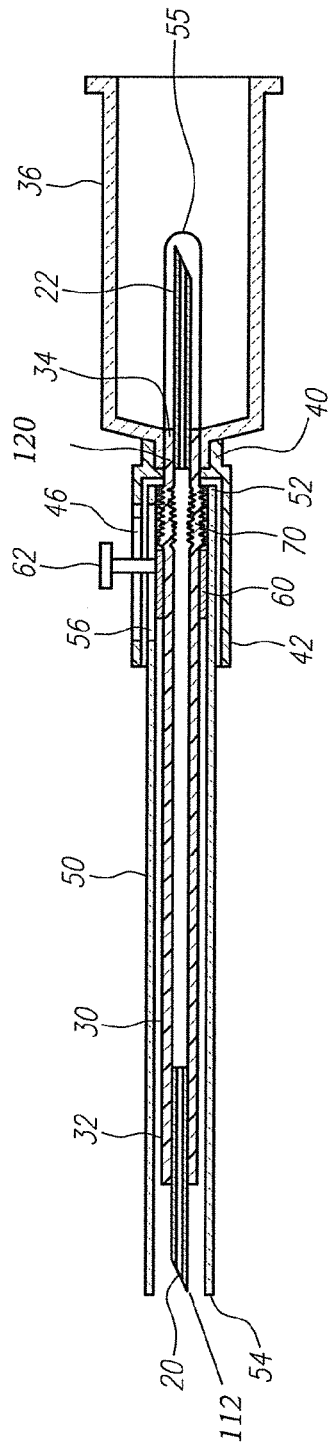
FIG. 3
FIG. 4

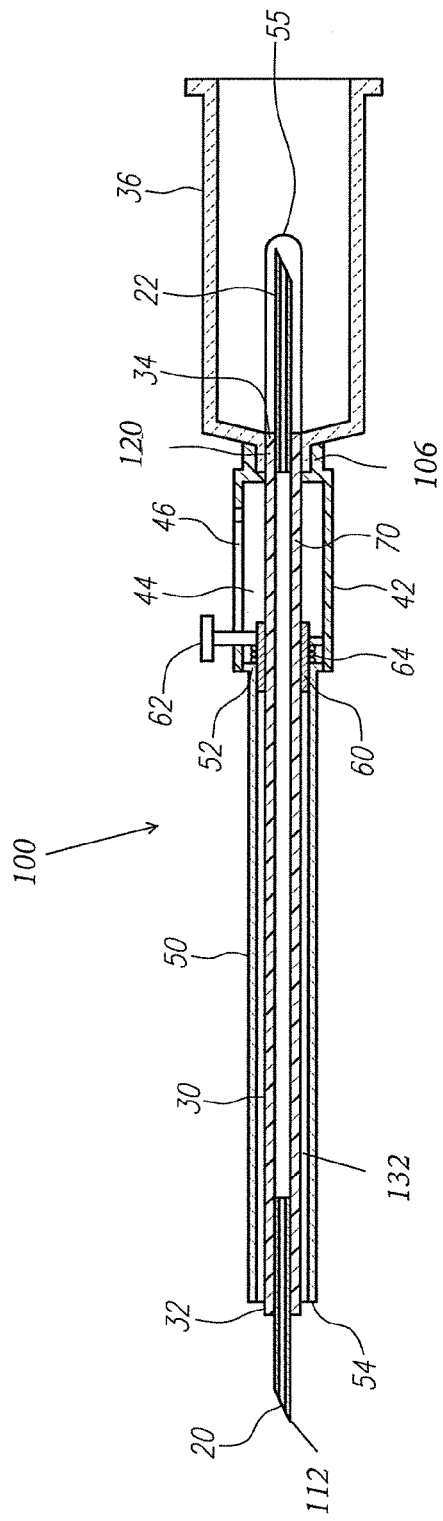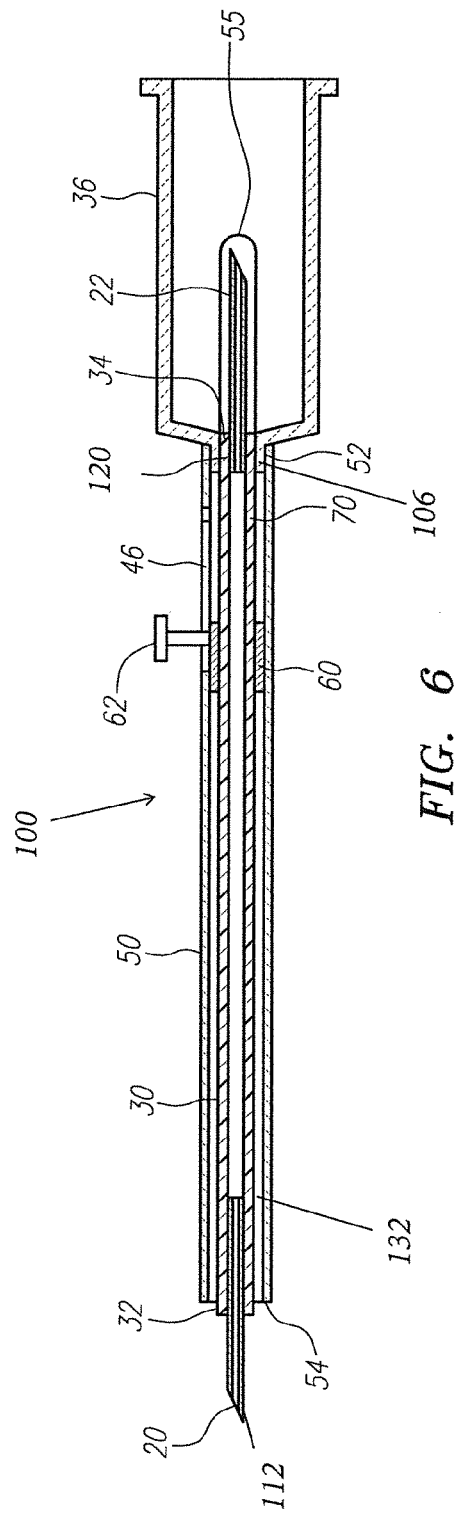

MEDICAL DEVICES WITH RETRACTABLE NEEDLE AND RELATED METHODS

FIELD OF ART

The present invention is generally directed to needle safety assemblies and related methods and more particularly to needle safety assemblies and related methods utilizing needle guards having unique mounting for low friction between the needle guard and the needle during needle movement, such as during retraction of the needle relative to the needle guard.

BACKGROUND

Insertion procedure for an intravenous (IV) catheter assembly contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand to stop the flow of blood through the catheter; and (4) the healthcare worker then tapes the exposed end of the catheter (the catheter hub) to the patient's skin and connects it to the source of the fluid to be administered into the patient's vein.

One problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick, which, under the circumstances, leaves the healthcare worker vulnerable to the transmission of various dangerous blood-borne pathogens, including AIDS and hepatitis.

Other needle types similarly expose healthcare workers to risks of accidental needle sticks. For example, a doctor administering an injection, using a straight needle, a Huber needle, an epidural needle, etc., may place the used needle on a tray for subsequent disposal by a nurse. For the period between placing the used needle on a tray or a work station to the time it is discarded, the used needle is a potential source for disease transmissions for those that work near or around the needle.

SUMMARY

The various embodiments of a blood collection device have several features, no single one of which is solely responsible for their desirable attributes. Without limiting the scope of the present embodiments as set forth in the claims that follow, their more prominent features now will be discussed briefly.

An aspect of the present disclosure include a medical device comprising: a needle attached to a elongate tube; an elongate shield extending over at least a portion of a length of the elongate tube, a distal end of the elongate shield spaced a first distance from a distal tip of the needle in an extended position; a needle holder coupled to the elongate shield and the elongate tube; and a tab extending radially outwardly from the elongate tube, the tab moving distally to retract the needle at least the first distance to a retracted position.

The medical device wherein a proximal end of the elongate tube can be prevented from moving proximally with the tab so that a flexible portion of the elongate tube between the tab and the proximal end is compressed when the tab is moved proximally.

The medical device wherein the flexible portion of the elongate tube can be more elastic than another portion of the elongate tube between the tab and a distal end of the elongate tube.

The medical device wherein the flexible portion of the elongate tube can have one or more notches to weaken the proximal portion.

The medical device wherein the flexible portion of the elongate tube can have a bellows shaped design to allow the portion to compress longitudinally.

The medical device can further comprise a housing coupled to the needle holder and having a housing slot extending at a length at least as long as the first distance, wherein the tab extends through the housing slot.

The medical device wherein a notch can extend from the proximal end of the housing slot to secure the tab.

The medical device wherein the housing has a housing chamber and wherein the housing chamber can have a diameter sized and configured to accommodate the portion of the elongate tube when the tab is moved proximally.

The medical device can further comprise a shield slot in the elongate shield, the shield slot can extend a length at least as great as the first distance and aligned with the housing slot, wherein the tab can extend through both the shield slot and the housing slot.

The medical device can further comprise another needle extending proximally into the needle holder and in fluid communication with the elongate tube.

Another feature of the present disclosure is a medical method using a blood collection device. The method can comprise: providing the blood collection device, the blood collection device comprising a needle attached to an elongate tube, an elongate shield extending over at least a portion of a length of the elongate tube, a distal end of the elongate shield spaced a first distance from a distal tip of the needle in a first position, a needle holder coupled to the elongate shield and the elongate tube, and a tab extending radially outwardly from the elongate tube; and moving the tab proximally along the slot so as to retract the needle into the shield.

The medical method can further comprise compressing a flexible portion of the elongate tube, the flexible portion extending approximately between the tab and a proximal end of the elongate tube.

The medical method can further comprise sliding the tab into a notch of a housing surrounding the flexible portion to secure the tab.

Still another aspect of the present disclosure is a blood collection device comprising: an elongate needle; a shield encompassing at least a portion of a length of the elongated needle, a distal end of the shield is spaced a first distance from a distal tip of the elongate needle in a first position; and wherein an axial length of a flexible portion of the elongate needle is capable of decreasing until the distal tip of the elongate needle is completely retracted into the shield by at least the first distance.

The blood collection device wherein the flexible portion can be more elastic than an adjacent portion of the elongate needle.

The blood collection device wherein the flexible portion can have one or more notches to weaken the collapsible portion.

The blood collection device wherein the flexible portion can have a different diameter than the other portion of the elongate needle so that the flexible portion can slide inside the adjacent portion or the adjacent portion can slide into the flexible portion when the distal tip of the elongate needle is retracted into the shield.

The blood collection device can further comprise a housing having a diameter sized and configured to accommodate the flexible portion.

The blood collection device can further comprise a tab extending from the elongate needle, wherein the distal tip of the elongate needle can retract proximally into the shield by moving the tab proximally.

The blood collection device can further comprise a spring retracting the elongate needle proximally into the needle shield.

Yet another aspect of the present disclosure includes a medical device comprising: a needle attached to a tube; a shield encompassing at least a portion of a length of the tube, a distal end of the shield is spaced a first distance from a distal tip of the needle in a first position; and wherein a length of the tube decreases at least a first distance to retract the needle into the elongate shield.

The medical device wherein the length of the tube can decrease at a flexible portion of the tube.

A yet additional aspect of the present disclosure is a needle safety assembly comprising: a needle with a sharpened tip attached directly or indirectly to a flexible tube portion having a proximal end that is constrained from proximal axial movement; an elongate shield comprising a distal end opening and a body with a lumen extending over at least a portion of the flexible tube portion with the distal end opening spaced a first distance from the sharpened tip in a needle extended position; a needle holder coupled directly or indirectly to the elongate shield and fixed axially relative to the elongate shield; said needle holder comprising a proximal opening sized and shaped to receive a sampling device; and a tab comprising a pin extending radially outwardly from within the lumen of the elongate shield and through a slot formed with the elongate shield, the tab being movable in a proximal direction to retract the needle tip in the proximal direction.

The needle safety assembly wherein the flexible tube portion can be located between a first end defined by the pin on the tab and a distal end of the needle holder, said flexible tube portion can have a weakened portion that shrinks in length when a compressive force is imparted by the tab.

The needle safety assembly can include an end axially aligned with the flexible tube portion and the end can be pressed fit within a bore of the needle holder and fixedly secured thereto.

The needle safety assembly can further comprise a socket assembly attached to the needle holder and the elongate shield.

The needle safety assembly can further comprise a vacutainer positioned in a proximal opening of the needle holder.

The needle safety assembly can further comprise a second needle having a sharpened tip extending in a proximal direction inside an interior cavity of the needle holder.

The needle safety assembly can further comprise a sleeve having a bore and a cylinder section aligned with the flexible tube portion located within the bore of the sleeve.

The needle safety assembly can further comprise an extension spring in biasing contact with the tab.

The needle safety assembly wherein the distal end opening of the elongate shield can be spaced a second distance from the sharpened tip in a needle retracted position; said second distance being smaller than the first distance.

The present disclosure also includes a method of manufacturing a needle safety assembly. The method can comprise: forming a needle holder with an interior cavity, a distal end, and a proximal end having an opening for receiving a sampling device in the interior cavity; attaching a needle having sharpened tip directly or indirectly to a flexible tube portion having a proximal end; fixing the proximal end of the flexible tube portion from axial displacement relative to the needle holder; attaching an elongate shield directly or indirectly to the needle holder, said elongate shield comprising a distal end opening and a body with a lumen; positioning the flexible tube portion within the lumen of the elongate shield so that the distal end opening of the elongate shield is spaced a first distance from the sharpened tip in a needle extended position; and extending a pin on a tab radially from within the lumen of the elongate shield through a slot formed with the elongate shield; said tab being movable in a proximal direction to move the needle tip in the proximal direction.

The method can further comprise attaching a second needle having a sharpened tip in the interior cavity of the needle holder.

The method can further comprise press fitting the proximal end of the flexible tube portion into a receiving bore at the distal end of the needle holder.

The method can further comprise placing a sleeve attached to the pin around a cylinder section aligned with the flexible tube portion so that the flexible tube portion is movable when moving the tab in the proximal direction.

The method can further comprise an elongate tube attached to the flexible tube portion.

The method can further comprise attaching a socket assembly to the needle holder and attaching the elongate shield to the socket assembly.

The method can further comprise a housing slot formed with the socket assembly and wherein the slot on the elongate shield has a portion that is aligned with the housing slot.

BRIEF DESCRIPTION OF THE DRAWINGS

These and other features and advantages of the present devices, systems, and methods will become appreciated as the same becomes better understood with reference to the specification, claims and appended drawings wherein:

FIG. 1 is an isometric view of an embodiment of a medical device or needle safety assembly having a retractable needle having features in accordance with the present disclosure;

FIG. 2 is a top view of the medical device or needle safety assembly of FIG. 1;

FIG. 3 shows a cross sectional view of the medical device or needle safety assembly of FIG. 1 in an extended position;

FIG. 4 shows a cross sectional view of the medical device or needle safety assembly of FIG. 1 in a retracted position;

FIG. 5 shows a cross sectional view of another embodiment of a medical device or needle safety assembly; and FIG. 6 shows a cross sectional view of yet another embodiment of a medical device or needle safety assembly.

DETAILED DESCRIPTION

The detailed description set forth below in connection with the appended drawings is intended as a description of the presently preferred embodiments of needle safety assemblies in which a needle is retracted into a safety shield in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

FIGS. 1-4 depict an embodiment of a needle safety assembly in the context of a blood collection set. The blood collection set includes or comprises an Intravenous (IV) needle cannula for insertion into a patient's blood vessel with an elongate tube, which can be a flexible tube, attached to and extending from the needle cannula. A second needle cannula, also attached to the other end of the flexible tube, is used to pierce or couple to a sampling device, such as a septum of an evacuated blood collection tube or a vacutainer, so that blood is transferred via the two needles and the tube into the sampling device, such as into the tube of the vacutainer.

With reference initially to the needle safety assembly 100 of FIGS. 1 and 2, a needle hub 36 having a needle 20 extending in a distal direction are shown in front perspective and side views. The needle safety assembly 100 comprises a guard assembly 102 comprising an elongate shield 50 attached to a socket assembly 40 comprising a housing body 42. In one example, the housing body 42 of the socket assembly 40 is unitarily formed to the holder body 104 of the needle holder 36. In alternative embodiments, as further discussed below, the elongate shield 50 can attach directly to the needle holder 36. In another example, the housing body 42 is separately formed and subsequently attached to a nose section 106 of the holder body 104, such as by interference fit, threaded engagement, bonding, welding, or combinations thereof. A vacutainer or sampling device 80 for collecting blood or other fluids is shown inserted into a proximal end 108 of the needle holder 36 and into the interior cavity thereof. Also shown in FIGS. 1 and 2 is a distal end 32 of an elongate tube 30 (FIG. 3), which secures the needle 20 to the needle holder 36, as further discussed below. In some examples, a notch or viewing window 21 may be incorporated with the needle 20, such as through the needle wall to expose part of the needle lumen. The notch 21 can be sealed, such as by a transparent or semi-transparent biocompatible material, to enable viewing of blood flashback through the needle lumen, which indicates that the needle is properly placed within a patient's vasculature. The biocompatible material can have a magnifying effect, a luminous effect, and/or made of a chromogenic polymer.

The housing body 42 of the socket assembly 40 has a housing slot 46 comprising a primary channel 110 and a notch 48. As shown, the primary channel 110 is generally parallel to the lengthwise axis of the elongate shield 50 and the notch 48, which is shorter lengthwise than the primary channel, is positioned generally orthogonally to the primary channel with other angular alignment contemplated. A tab 62 comprising a pin and a head or knuckle is disposed within the housing slot 46 for controlled movement within the housing slot. As further discussed below, the pin of the tab 62 extends radially through the slot 46. The tab 62 is attached to a sleeve 60 (FIG. 3) which is attached to the elongate tube 30 for moving the elongate tube 30 when moving the tab. In alternative embodiments, the sleeve 60 is omitted and the flexible tube 40 is formed with a bearing section for connecting to a pin on the tab 62. This allows the tab 62 to move the pin that attaches directly to the bearing surface without a separate sleeve. Unless the context indicates otherwise, the various components may be made from convention materials.

With reference now to FIGS. 3 and 4 in addition to FIGS. 1 and 2, the needle 20 with a sharpened tip 112 may be referred to as a first needle or distal needle to be distinguished from a second needle or proximal needle 22 having a sharpened tip 114 for puncturing a septum of a vacutainer or sampling device. The first needle 20 is attached to a distal end 32 of an elongate tube 30 and a proximal end 120 of the elongate tube 30 is attached to a blunt distal end of the second needle 22. The elongate tube 30 can include other sections and the needle(s) can attach directly or indirectly to the elongate tube via other sections. The proximal end 120 of the elongate tube 30 is attached to the nose section 106 of the holder body 104. In an example, the proximal end 120 is pressed fit into a bore of the nose section 106. The proximal or second needle 22 is arranged so that its blunt distal end is pressed into the bore of the tube 30 and its sharpened proximal end 114 is disposed in an interior cavity 122 of the holder body 104 for piercing a septum on a vacutainer. As previously discussed, the socket assembly 40 may be unitarily formed with the needle holder 36. In the example shown, the socket assembly 40 has a coupling end 130 for attaching to the nose section 106 of the needle holder 36. The various connections at the nose section 106 are made by interference fit. Alternatively or in addition thereto, adhesive, bonding, welding, or combinations thereof may be used to secure the various components at the nose section.

The elongate tube 30 is partially or completely surrounded by the elongate shield 50, which is fixed axially relative to the socket assembly 40 and the needle holder 36. A sleeve 60 is provided in the annular space between the elongate shield 50 and the elongate tube 30. As shown, the sleeve 60 is attached to a shaft, stem, or pin 126 on the tab 62 and the sleeve is movable with the tab. In an example, the sleeve 60 and the tab 62 are unitarily formed. In other examples, the sleeve 60 and the tab 62 are separately formed and subsequently attached to one another, such as by threaded engagement, bonding, gluing, welding, interference fit, or combinations thereof. The elongate tube 30 passes through the bore of the sleeve 60 and the two are fixedly secured to one another. The elongate tube 30 comprises a flexible portion 70 proximal of the sleeve 60. As further discussed below, the flexible portion 70 is configured to collapse in length, buckle, or shrink in length when axially compressed to recess the first needle 20 within the elongate shield 50. Thus, the elongate tube, the elongate shield, or both the elongate tube and the elongate shield have proximal ends that are constrained or fixed from proximal axial movement. The elongate tube has a cylinder end section that is constrained at the proximal end so that the flexible tube portion 70 can be pressed against the constrained end to shrink the length of the flexible tube portion 70.

The first needle 20 is configured for puncturing and drawing blood from the vein of a patient. The first needle 20 is made of a hard biocompatible material, such as metal or hard plastic, and is bonded or press fitted into a lumen of the elongate tube 30, in particular to the distal end opening of the elongate tube 30. In one embodiment, the first needle 20 is an extension of the elongate flexible tube 30 with a sharp tip for puncturing and accessing the vein.

The needle holder 36 is configured to receive blood drawn from the patient. In one example, a vacutainer 80 (FIGS. 1 and 2) is received in the open proximal end and in the interior cavity 122 of the needle holder 36 to store the drawn blood. In another example, the needle holder 36 can have a connection end for receiving another medical device, such as a sampling device. For example, the needle holder 36 can have a female Luer taper, with or without external threads, to receive a Luer connector or adaptor of a sampling device.

The elongate shield 50 is coupled to the needle holder 36 via the socket assembly 40. The elongate shield 50 extends from a proximal end 52 within the interior chamber or cavity 44 of the socket assembly 40 to a distal end 54 at or adjacent the distal end 32 of the flexible tube 30. The elongate shield 50 is sized and shaped to surround the elongate tube 30, for example the elongate tube is located in the lumen of the elongate shield, in a ready position (FIG. 3) with the needle tip 112 extending distally of the distal end 54 of the shield 50 a first distance. The distal end 32 of the elongate tube 30 extends distally of the distal end 54 of the shield 50 but can extend short of the distal end 54 of the shield. As shown, a gap or space 132 is provided between the elongate shield 50 and the elongate flexible tube 30. The gap or space 132 provides clearance for the elongate flexible tube 30 to freely slide within the elongate shield 50. In some examples, two thousandths to about eight thousandths total clearance is provided at the gap 132 with other range, for example 40 thousandths clearance, contemplated. The exterior of the elongate tube 30 may be provided with spaced apart ridges or projections to take up all or part of the gap 132 and to act as bearings when the tube 30 slides relative to the shield 50. In the illustrated embodiment, the elongate shield 50 is spaced from the flexible tube 30 by a distance that is at least a thickness of the housing sleeve 60.

With specific reference to FIG. 3 in addition to FIGS. 1 and 2, a housing slot 46 is formed with the housing body of the socket assembly 40, which has a primary channel 110 and a notch 48, as previously discussed. An elongate slot 56 is formed in or with the shield 50 subjacent the primary channel 110 and aligned with primary channel 110 of the housing slot 46. The pin 126 on the tab 62 extends radially through the elongate slot 56 and the primary channel 110 from the housing sleeve 60. Although the tab, and particularly the pin, extends directly from the sleeve, the pin is understood to extend radially outwardly from the elongate tube, which is located inside the sleeve. In some examples, the sleeve 60 is configured to grip a surface, such as an elongated section, for example a cylindrical section, that is axially aligned with the flexible tube portion 70 of the elongate tube to move that surface against the flexible tube portion to buckle, collapse, or shrink the length of the flexible portion without having to directly grip and move the flexible portion. For example, the sleeve 60 can grip a coupling or a cylinder section that is in turn attached to the first needle and to the flexible tube portion. By moving the coupling or cylinder section proximally, the flexible tube portion can be shrunk in length by pressing a proximal end of the flexible tube portion against a secured proximal end without having to directly grip the elongate tube or the flexible tube portion. Thus, the flexible tube portion can be located between the tab 62, such as a sleeve attached to the tab, and a distal end of the needle holder and be compressed or shrunk in length when the tab is moved in the proximal direction to apply a compressive load on the flexible tube portion.

The housing slot 46 and the elongate slot 56 are configured for guiding the pin 126 on the tab 62 to slide from a distal or extended position as shown in FIGS. 1-3, to a proximal or retracted position as shown in FIG. 4. At the retracted position, the tip of the first needle and the distal end opening of the elongate shield is at a second distance, which is less than a first distance. The two slots 46, 56 have portions that align to allow movement of the pin 126 through the aligned portions. In the distal or extended position, the first needle 20 is exposed for performing a medical procedure, such as to access the vein of the patient. In the proximal or retracted position shown with reference to FIG. 4, the first needle 20 is retracted in the elongate shield 50 to prevent accidental contact with the first needle 20. In some examples, the distal end of the elongate shield 50 is equipped with a seal, a valve or a coagulating agent to prevent or limit blood from dripping out the first needle 20 when in the proximal or retracted position.

The notch 48 extends from a proximal end of the housing slot 46 to restrict or hold the pin 126 on the tab 62. For example, when the pin 126 is held at the notch 48, distal axial movement is prevented by the wall structure of the notch. The tab 62 can be manipulated by a user following a medical procedure to slide axially in the proximal direction and then radially to engage the notch 48. When the tab 62 moves in the proximal direction, it moves the sleeve 60 in the proximal direction. As the flexible tube 30 is attached to the sleeve 60, such as by gluing, adhesive, detents, threads, or combinations thereof, the tube 30 is gripped by the sleeve 60 and pressed in the proximal direction against the constrain of the proximal end 120 of the tube. This causes the flexible portion 70 of the tube 30 to collapse, such as shrink in length, as shown in FIG. 4, to enable proximal movement of the distal end 32 of the tube and hence the first needle 20 inside the distal opening the shield 50. In the proximal or retracted position shown in FIG. 4, the tab 62 engages the notch 48 to prevent the flexible tube 30 from expanding or recoiling at the collapsed flexible portion 70 to move the first needle 20 back to the exposed needle position of FIG. 3. In other examples, other breaking feature for preventing re-emergence of the needle out the distal opening of the elongate shield 50 is employed, such as internal detents. In other embodiments, a distal notch, similar to the proximal notch 48, is provided at the distal end of the primary channel 110 having a radial portion to hold the first needle 20 in the extended position.

In one embodiment, the second needle 22 is provided with a multi-sampling Luer adaptor (MSLA) 55. The MSLA 55 is a generally elongated rubber or elastomer having a central lumen for receiving the second needle 22 therein. The MSLA 55 can have an enlarged distal end that serves to anchor the MSLA 55 at or near a distal end 38 of the needle holder 36. In its normal expanded state, the MSLA 55 covers sharpened tip 114 of the second needle 22. However, upon pushing a septum of the vacutainer 80 against the tip of the MSLA 55, the MSLA collapses and the second needle 22 is exposed to then puncture the septum to form fluid communication between the second needle 22 and the interior of the vacutainer 80. The vacuum or lower pressure inside the vacutainer 80 assists in drawing blood through the medical device 100. Upon removal of the vacutainer 80, the MSLA 55 expands and again covers the second needle 22. In some examples, the MSLA 55 is omitted.

Referring specifically to FIG. 4, in use, once blood collection in the vacutainer 80 is complete, the clinician may remove the first needle 20 from the patient by pulling the tab 62 so that the tab 62 translates proximally along the housing slot 46 relative to the socket assembly 40. Alternatively, the entire needle safety assembly 100 is moved away from the patient to remove the first needle 20 from the patient before activating the safety feature on the needle safety assembly. During movement of the tab 62, the needle 20 is also drawn proximally, as previously discussed. Preferably the housing slot 46 is of sufficient length so that when the tab 62 is moved proximally the needle 20 is retracted completely into the shield 50 so that the sharpened tip 112 of the first needle is even with or recessed from the distal opening 54 of the elongate shield 50. In one example, the length of the primary channel 110 of the housing slot 46 is at least the same as or greater than the length or distance between the tip 112 of the first needle 20 and the distal end of the elongate shield 50 to ensure proper coverage of the first needle 20 inside the elongate shield 50 when the tab 62 is activated or manipulated to move from a distal position to a proximal position. Once in the proximal position, the pin 126 on the tab 62 is slid into the proximal notch 48 on the housing slot 46. In an example, the proximal notch 48 has a reduced section for firmly securing the pin within the notch 48 to deter or prevent re-use, such as to move the tab back to the distal position to re-expose the first needle 20. Similarly, the elongate slot 56 on the shield 56 should have a length at least as long as the housing slot 46 but optionally can be longer.

In the illustrated embodiment, as the tab 62 is urged proximally and the sleeve 60 moves the tube 30 against a dead-end, a fixed structure, or against a grip of another structure, the flexible portion 70 of the elongate tube 30 is longitudinally shortened. As previously described, the proximal end 120 of the tube 30 is restrained at the nose section 106 of the needle holder 36. In some examples, the proximal end of the flexible tube portion 70 is aligned with another portion or section and that other portion or section restrained from proximal axial movement. Thus, the flexible tube portion 70 of the elongate tube 30 collapses, folds, bends, or otherwise shrink in length when the tab 62 moves proximally to retract the first needle 20 into the elongate shield 50. Preferably the interior chamber 44 of the socket assembly 40 has a bore diameter or volume sufficient to accommodate the flexible portion 70 as it collapses, folds, bends or otherwise shrink in length. In some embodiments, the flexible portion 70 has a thinner wall, one or more notches or weakened sections, or a bellows shaped design to facilitate collapsing the flexible portion 70 of the elongate tube 30, similar to an accordion. In another embodiment, the flexible portion 70 may have different flexural properties than the other portions of the flexible tube 30, such as between the housing sleeve 60 and the distal end 32 of the flexible tube 30, to facilitate collapsing, buckling, or otherwise shrink in length. In an example, the first needle 20 has a length that extends to or near where the tab 62 attaches to the elongate tube 30. Thus, in the alternative embodiment, the elongate tube 30 distal of the tab 62 is omitted and the first needle extends to where the tab enters the slot of the elongate tube. Alternatively, the first needle is attached to an elongated cylinder, which is coupled to the sleeve or directly to the tab and the end of the elongated cylinder is axially aligned with a flexible tube portion 70.

Referring now to FIG. 5, an alternative needle safety device 100 is shown in a ready to use position. The present needle safety device 100 is similar to the device of FIGS. 1-4 with the following differences. In the present embodiment, the elongate shield 50 is integrated with the socket assembly 40. For example, the elongate shield 50 forms part of, such as unitarily or integrally formed to, the socket assembly 40. Thus, the proximal end 52 of the elongate shield 50 is distal of the housing slot 46 and the tab 62 and not attached to a socket of the needle holder. That is, the shield 50 is coupled directly to the distal end of the housing body 42 and not the needle holder. Thus, in the present embodiment, the tab does not project through the elongate shield 50 and a slot formed through the elongated shield to accommodate the pin on the tab is not required. The tab 62, and more particularly the pin 126 on the tab, extends radially from inside a lumen and through the housing slot 46. In the present embodiment, the flexible portion 70 of the flexible tube 30 has more interior space in the interior chamber 44 of the socket assembly to collapse when the first needle 20 is retracted inside the elongate shield 50.

In the alternative embodiment of FIG. 5, the housing body 42 of the socket assembly 40 can be made smaller relative to the embodiment of FIGS. 1-4, such as smaller in ID and/or OD. In an example, components are added to aid in collapsing of the flexible portion 70 of the elongate tube 30 or to prevent leaks. In one example, an extension spring 64 is positioned in the interior cavity 44 of the socket assembly 40 to bias the sleeve 60 or the tab 62 in the proximal direction. Thus, upon moving the pin 126 from a distal notch on the housing slot 46, the spring assists in moving the tab in the proximal direction, which assists in shrinking the length of the flexible tube portion. In an alternative embodiment, a compression spring is provided in the interior cavity 44 of the socket housing to resist inadvertent movement of the tab in the proximal direction. Thus, an intentional force is required to overcome the compression spring to move the tab to the proximal position to collapse the flexible tube portion.

Thus, the present disclosure is understood to include a needle safety assembly comprising a needle with a sharpened tip attached directly or indirectly to a flexible tube portion having a proximal end that is constrained from proximal axial movement; an elongate shield comprising a distal end opening and a body with a lumen extending over at least a portion of the flexible tube portion with the distal end opening spaced a first distance from the sharpened tip in a needle extended position; a needle holder coupled directly or indirectly to the elongate shield and fixed axially relative to the elongate shield; said needle holder comprising a proximal opening sized and shaped to receive a sampling device; and a tab comprising a pin extending radially outwardly from within the lumen of the elongate shield and through a slot formed with the elongate shield, the tab being movable in a proximal direction to retract the needle tip in the proximal direction.

With reference now to FIG. 6, another embodiment of a needle safety assembly 100 is shown, which is similar to the needle safety assembly 100 of FIGS. 1-4 with the following differences. In the present embodiment, the elongate shield 50 extends directly to the needle holder 36 and is attached directly to the nose section 106 of the needle holder. Thus, in the present embodiment, the socket assembly 40 is eliminated and the elongate shield 50 couples directly to the nose section 106 of the needle holder 36 without a separate socket assembly. The tab 62 extends from the sleeve 60 through the slot 46 formed with the elongate shield. The slot 46 on the elongate shield 50 is provided with a primary channel 110 and at least one proximal notch 48 with a distal notch contemplated. In other examples, the proximal notch is eliminated and other holding means, such as internal detents, is provided to prevent distal movement of the tab.

In another embodiment, two or more tabs 62 may be provided with the elongate tube 30 to increase the number of tabs and/or locations that a user may grab to manipulate the device to cover the needle tip or omit all tabs 62. In still other embodiments, there is no elongate tube 30 or flexible portion 70 between the sleeve 60 and the distal end 38 of the needle holder 36. Instead, the housing chamber or interior 44 is sealed so that blood can flow therethrough, for example to the vacutainer 80 in the needle holder 36. In other embodiments, the elongate tube 30 reduces to a needle tip at the distal end 32, thereby eliminating the need for a separate first needle 20.

Thus, the present disclosure is understood to include a needle safety assembly comprising a needle with a sharpened tip attached directly or indirectly to a flexible tube portion having a proximal end that is constrained from proximal axial movement; an elongate shield comprising a distal end opening and a body with a lumen extending over at least a portion of the flexible tube portion with the distal end opening spaced a first distance from the sharpened tip in a needle extended position; a needle holder coupled directly or indirectly to the elongate shield and fixed axially relative to the elongate shield; said needle holder comprising a proximal opening sized and shaped to receive a sampling device; and a tab comprising a pin extending radially outwardly from within the lumen of the elongate shield and through a slot formed with the elongate shield, the tab being movable in a proximal direction to retract the needle tip in the proximal direction.

Although the figures show several medical devices or blood collection devices having a second needle 22, it is understood that the principles discussed herein can be employed in other types and embodiments of medical devices, which may or may not include a second needle 22, and which may have somewhat different structures. Also, methods of manufacturing and of using the devices and assemblies discussed elsewhere herein are within the scope of the present disclosure.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or sub-combinations of the specific features and aspects of the disclosed embodiments may be made and still fall within the scope of the inventive subject matter. Further, it should be understood that various features and aspects of the disclosed embodiments can be combined with or substituted for one another in order to form varying modes of the disclosed inventive subject matter and in fact contemplated provided the combinations do not conflict. Thus, it is intended that the scope of the inventive subject matter herein disclosed should not be limited by the particular disclosed embodiments described above, but should be determined only by a fair reading of the claims that follow.

What is claimed is:

1. A needle safety assembly, comprising:
    a needle with a sharpened tip attached directly or indirectly to a flexible tube portion, said flexible tube portion having a proximal end that is constrained from proximal axial movement;
    an elongate shield comprising a distal end opening and a body with a lumen extending over at least a portion of the flexible tube portion with the distal end opening spaced a first distance from the sharpened tip in a needle extended position;
    a needle holder coupled directly or indirectly to the elongate shield and fixed axially relative to the elongate shield; said needle holder comprising a proximal opening sized and shaped to receive a sampling device;
    a tab comprising a pin extending radially outwardly from within the lumen of the elongate shield and through a slot formed with the elongate shield, all of the tab being movable in a proximal direction to retract the needle tip in the proximal direction; and
    a second needle having a sharpened tip extending in a proximal direction inside an interior cavity of the needle holder.

2. The needle safety assembly of claim 1, wherein the flexible tube portion is located between a first end defined by the pin on the tab and a distal end of the needle holder, said flexible tube portion has a weakened portion that shrinks in length when a compressive force is imparted by the tab.

3. The needle safety assembly of claim 1, wherein an end axially aligned with the flexible tube portion is pressed fit within a bore of the needle holder and fixedly secured thereto.

4. The needle safety assembly of claim 1, further comprising a socket assembly attached to the needle holder and the elongate shield, said socket assembly comprising a housing slot and wherein the slot on the elongate shield has a portion aligned with the housing slot.

5. The needle safety assembly of claim 1, further comprising a vacutainer positioned in a proximal opening of the needle holder.

6. The needle safety assembly of claim 1, wherein the second needle is in fluid communication with the needle and the flexible tube portion.

7. The needle safety assembly of claim 1, further comprising a sleeve having a bore and a cylinder section aligned with the flexible tube portion located within the bore of the sleeve.

8. The needle safety assembly of claim 1, further comprising an extension spring in biasing contact with the tab.

9. The needle safety assembly of claim 1, wherein the distal end opening of the elongate shield is spaced a second distance from the sharpened tip in a needle retracted position; said second distance being smaller than the first distance.

10. A method of manufacturing a needle safety assembly comprising:
    forming a needle holder with an interior cavity, a distal end, and a proximal end having an opening for receiving a sampling device in the interior cavity;
    attaching a needle having sharpened tip directly or indirectly to a flexible tube portion having a proximal end;
    fixing the proximal end of the flexible tube portion from axial displacement relative to the needle holder;
    attaching an elongate shield directly or indirectly to the needle holder, said elongate shield comprising a distal end opening and a body with a lumen;
    positioning the flexible tube portion within the lumen of the elongate shield so that the distal end opening of the elongate shield is spaced a first distance from the sharpened tip in a needle extended position;
    extending a pin on a tab radially from within the lumen of the elongate shield through a slot formed with the elongate shield; all of said tab and pin being movable in a proximal direction to move the needle tip in the proximal direction; and
    attaching a second needle having a sharpened tip in the interior cavity of the needle holder.

11. The method of claim 10, further comprising placing the second needle in fluid communication with the flexible tube portion.

12. The method of claim 10, further comprising press fitting the proximal end of the flexible tube portion into a receiving bore at the distal end of the needle holder.

13. The method of claim 10, further comprising placing a sleeve having a bore attached to the pin around a cylinder section so that said cylinder section is located inside the bore, said cylinder section aligned with the flexible tube portion and the flexible tube portion is movable when moving all of the tab in the proximal direction.

14. The method of claim 10, further comprising an elongate tube attached to the flexible tube portion and to the needle.

15. The method of claim 10, further comprising attaching a socket assembly to the needle holder and attaching the elongate shield to the socket assembly.

16. The method of claim 15, further comprising a housing slot formed with the socket assembly and wherein the slot on the elongate shield has a portion that is aligned with the housing slot.

* * * * *